US006152140A

United States Patent [19]

Blum

[11] Patent Number: 6,152,140

[45] Date of Patent: Nov. 28, 2000

[54] PHYSIO/ENERGETIC THERAPEUTIC METHOD AND INTERACTIVE MONITORING DEVICE

[76] Inventor: Jeanne Elizabeth Blum, Haikuleana, 555 Rd., Haiku, Hi. 96708-5884

[21] Appl. No.: 08/883,284

[22] Filed: Jun. 27, 1997

[51] Int. Cl.[7] .......... A61B 19/00

[52] U.S. Cl. .......... 128/898; 128/907; 600/548; 606/204

[58] Field of Search .......... 128/898, 907; 600/548; 606/204

[56] References Cited

U.S. PATENT DOCUMENTS

| | | | |
|---|---|---|---|
| 3,894,532 | 7/1975 | Morey | 600/547 |
| 3,900,020 | 8/1975 | Lock | 600/548 |
| 3,908,669 | 9/1975 | Man et al. | 607/74 |
| 4,016,870 | 4/1977 | Lock | 600/548 |
| 4,160,447 | 7/1979 | Teshima et al. | 600/548 |
| 4,180,079 | 12/1979 | Wing | 607/69 |
| 4,232,678 | 11/1980 | Skovajsa | 607/89 |
| 4,267,838 | 5/1981 | McCall | 606/204 |
| 4,319,584 | 3/1982 | McCall | 607/136 |
| 4,408,617 | 10/1983 | Auguste | 600/548 |
| 4,446,870 | 5/1984 | Wing | 607/72 |
| 4,450,846 | 5/1984 | McCall | 607/136 |
| 4,535,784 | 8/1985 | Vojtech et al. | 600/548 |
| 4,759,718 | 7/1988 | Nobuta | 434/262 |
| 4,981,146 | 1/1991 | Bertolucci | 607/72 |
| 5,261,422 | 11/1993 | Kelly | 128/898 |
| 5,385,150 | 1/1995 | Ishikawa | 600/548 |

*Primary Examiner*—Dinh X Nguyen

*Attorney, Agent, or Firm*—Mitchell A. Stein

[57] ABSTRACT

A physio/energetic therapeutic method for articulating various acupressure points in a specific sequence, in which these points have been heretofore “forbidden” because of the risk of termination of pregnancy, involving three sets of points that are articulated in the first three days of a woman’s period, for 3 to 5 minutes for each point, per day, in order to regulate problematic menstrual cycles by having a clearing effect on the next cycle, thereby eliminating build-up in the body which leads to PMS and cramps, and in the case of endometriosis, back flow and back-up of energy. Also shown are various acupressure point therapies for generally minimizing the effects of PMS and edema, maximizing the chances of contraception in a woman, and minimizing the chances of miscarriage or abnormal uterine bleeding. An interactive monitoring device is also shown for storing, identifying and retrieving information relative to the treatment therapies.

4 Claims, 17 Drawing Sheets

PHYSIO/ENERGETIC THERAPEUTIC METHOD AND INTERACTIVE MONITORING DEVICE

FIELD OF THE INVENTION

The present invention relates to the field of therapeutic methods and processes for regulating bodily functions through the application of pressure to various external points on the human anatomy in accordance with a specific, repeated regime. More particularly, the invention relates to stimulation of energy flows by articulation of precise, predetermined points in a specific sequence in a manner intended to improve the physical state of the body, including balancing and regulating womens' menses and reproductive cycles.

BACKGROUND OF THE INVENTION

Since ancient times, chinese medical practitioners have recognized the interconnection of mind, body and spirit and the direct and significant effect of this interconnection on physical healing. Western medicine, while challenged by the ancient Eastern concept of "invisible" energy flowing throughout the body, has done little to recognize the evidence of efficacy of these ancient concepts—although Hippocrates was the father of Western medicine, treated women with menstrual problems through ear piercing and the wearing of earings—or investigate the underlying concepts or techniques through, for example, the development of effective therapeutic techniques or devices that employ energy manipulation or redirection.

For example, Dr. Kim Bong Han of the University of Pyongang in North Korea discovered that the energy flows in the body are contained within thin membranes filled with colorless fluid. German doctors have found that when electricity is introduced at one point in the flow, it arrives at the target organ with which the point is associated. These flows were also noted by Sir Thomas Lewis as early as 1937, but he did not understand the significance or utility of his discovery. Stephen T. Chang, *The Great Tao* (San Francisco-:Tao Publishing, 1992), pp. 238, 239.

More recently, Kirlian photography has captured the healing energy emitted from the hands of healers and practitioners of Oriental medicine who work with this energy, or lack thereof. Certain people who possess unique sensitivity to this energy have reported that they actually "feel" the flows of energy in the body, and can even detect where and when blockages occur.

Students of Taoism were originally students of meditation, and were taught, through meditation, to activate energy points on their body through thought. Such "Taoist Masters" mastered this process, called activation. The next generation of students suffered problems with this approach. In order for this next generation to become effective practioners of the healing arts, accupressure was developed as a means to apply pressure to various points through physical touching, in order to thereby activate and control the body's energy flows. Thereafter, the next generation of practioners suffered problems in feeling the energy flows through their hands. Consequently, accupuncture was developed as a method of utilizing needles to physically apply stimulation to the known regions of the body where such stimulation was recognized as causing specific results. In this manner, students who suffered from an inability to meditate or to feel such energy points through their hands, could nonetheless perform recognized tasks through the application of acupressure and acupuncture techniques, respectively.

Acupuncturists have invaded the western front and are recognized by some of the medical community as satisfying a necessary element in overall medical treatment. In recent years, various aspects of Oriental medicine have begun to take a rightful place alongside allopathic (i.e., traditional Western) medical techniques and therapies. For example, when the situation warrants, it has been reported that surgeons in New York, Boston, Dallas and San Francisco have selectively introduced acupuncture in place of traditional (and often dangerous) anesthesia. Indeed, acupuncture-enhanced treatment for asthma has recently received governmental approval in the United States, and Dr. Oz of the Columbia Presbyterian Hospital in New York City, a world renowned heart surgeon, employs two female hands-on healers to stimulate acupressure points during surgery.

The historical growth of meditation, acupressure and acupuncture, while teaching the application of stimulation to certain points, has actually taught away from the application of stimulation to a group of various points deemed "forbidden," and in fact were known collectively as the Forbidden Pregnancy Points. Perhaps it was reluctance to interfere with normal female functioning or the birth cycle that lead to restrictions on articulation of various female-specific point sequences. This is because articulation of the so-called "forbidden" points on a pregnant women was known to lead to termination of pregnancy—often miscarriage in one to three days. Likely because of this result, and all of the ramifications associated therewith, that these points were banned from use. Thus, such points have, for many hundreds of years, remained essentially forbidden, and practitioners in the arts of acupressure and acupuncture have neither systematically employed them, nor studied the impact that they may have on non-pregnant women.

The inventor hereof, a woman and student of Taoism and the healing arts, could not help but conceive that for every negative there must be a positive—an essential yin/yang balance must even be found in the "forbidden" points. Thus, through study and employment of the "forbidden" points on herself and her clients, she has determined methods and systems directed to employing these points in a manner sought to: (a) regulate the menstrual cycle each month to rid one of the primary imbalance at the root of menstrual problems, which are the cause of the symptoms of "PMS" (including cramping, backache, physical pain, anxiety, irritability, mood swings, tension, bloating, fluid retention, weight gain, breast tenderness, craving for sweets, dizziness, fatigue, headache, increased appetite, palpitations, confusion, crying, depression, forgetfulness, insomnia, and withdrawal); (b) regulate or "bring on" a regular period each month that can also servew as a gentle and non-invasive form of birth control; and (c) stave off the onset of menopause through flushing-out and replenishing qualities, and even revere the menopausal process.

Also disclosed is a portable device aimed at both stimulating the needed points in specialized sequence in accordance with a preferred embodiment of the invention, as well as to keep track of the stimulation on a routine or daily basis.

Despite the western medical communities general failure to acknowledge eastern principles, others have invented devices for treatment of disease or articulation of acupressure/acupuncture points. For example, U.S. Pat. No. 5,261,422 to Kelly shows a process and device for treatment of disease employing electromagnetic oscillations (i.e., sound waves.) U.S. Pat. No. 4,160,447 to Teshima shows a device for detecting particular impedance of skin. U.S. Pat. No. 5,385,150 to Ishikawa shows an acupuncture device that electrically pulses acupuncture points. U.S. Pat. No. 4,759, 718 to Nobuta indicates a "training wear" which sets up cure target points. U.S. Pat. No. 4,981,146 to Bertolucci shows a nausea control device imparting electrical pulses to percardium six (P6) acupuncture point. U.S. Pat. No. 4,535,784 to Rohlicek, et al., shows an apparatus for stimulating acupuncture points by light radiation. Other electroacupuncture patents include U.S. Pat. No. 4,446,870 to Wing; U.S. Pat. No. 4,450,846 to McCall; U.S. Pat. No. 4,408,617 to Auguste; D273,706 to McCall; U.S. Pat. No. 4,319,584 to McCall; U.S. Pat. No. 4,267,838 to McCall; U.S. Pat. No. 4,232,678 to Skovajsa; U.S. Pat. No. 3,908,669 to Man, et al.; U.S. Pat. No. 4,180,079 to Wing, et al.; U.S. Pat. No. 3,894,532 to Morey; U.S. Pat. No. 4,016,870 to Lock; and U.S. Pat. No. 3,900,020 to Lock.

However, none of these patents, or the medical community, show the physio/energetic therapeutic method, process and interactive monitoring device of the subject invention, which seeks to employ articulation of certain "forbidden" points to, among other things, provide proper control over a woman's menstrual cycle.

SUMMARY OF THE INVENTION

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

The present invention relates to a physio/energetic therapeutic method for articulating various acupressure points in a specific sequence, in which these points have been heretofore "forbidden" because of the risk of termination of pregnancy, involving three sets of points that articulated in the first three days of a woman's period, for 3 to 5 minutes for each point, per day, to have a clearing out effect and a regulation and reduction of menstrual problems in the next bleeding (menstrual) cycle. in order to minimize the effects of menstruation. At absolute minimum, Large Intestine 4 and Spleen 6 should be worked a few times per day while the woman's period is in progress. Also shown are various acupressure point therapies for generally minimizing the effects of PMS and edema, maximizing the chances of contraception in a woman, and minimizing the chances of miscarriage or abnormal uterine bleeding. An interactive monitoring device is also shown for storing, identifying and retrieving information relative to the treatment therapies.

BRIEF DESCRIPTION OF THE DRAWINGS

The present invention is further described in detail below with reference to the accompanying drawing, in which.

DETAILED DESCRIPTION OF THE PREFERRED EMBODIMENTS

FIGS. 1 through 15 show acupressure points that are, for each figure, involved in the proper management of the organs identified. All points shown in each figure are currently articulated in the order presented to control the energy flow in the identified organ. Certain of these points are circled, to designate a series of points that have heretofore been taught to be avoided during pregnancy, and consequently have been generally avoided entirely. Thus, the total series of twenty-four so-called Forbidden Pregnancy Points have been avoided almost altogether for treatment for women, because of the heretofore considered expectation that articulation of such points would interfere with pregnancies.

Figure 16:
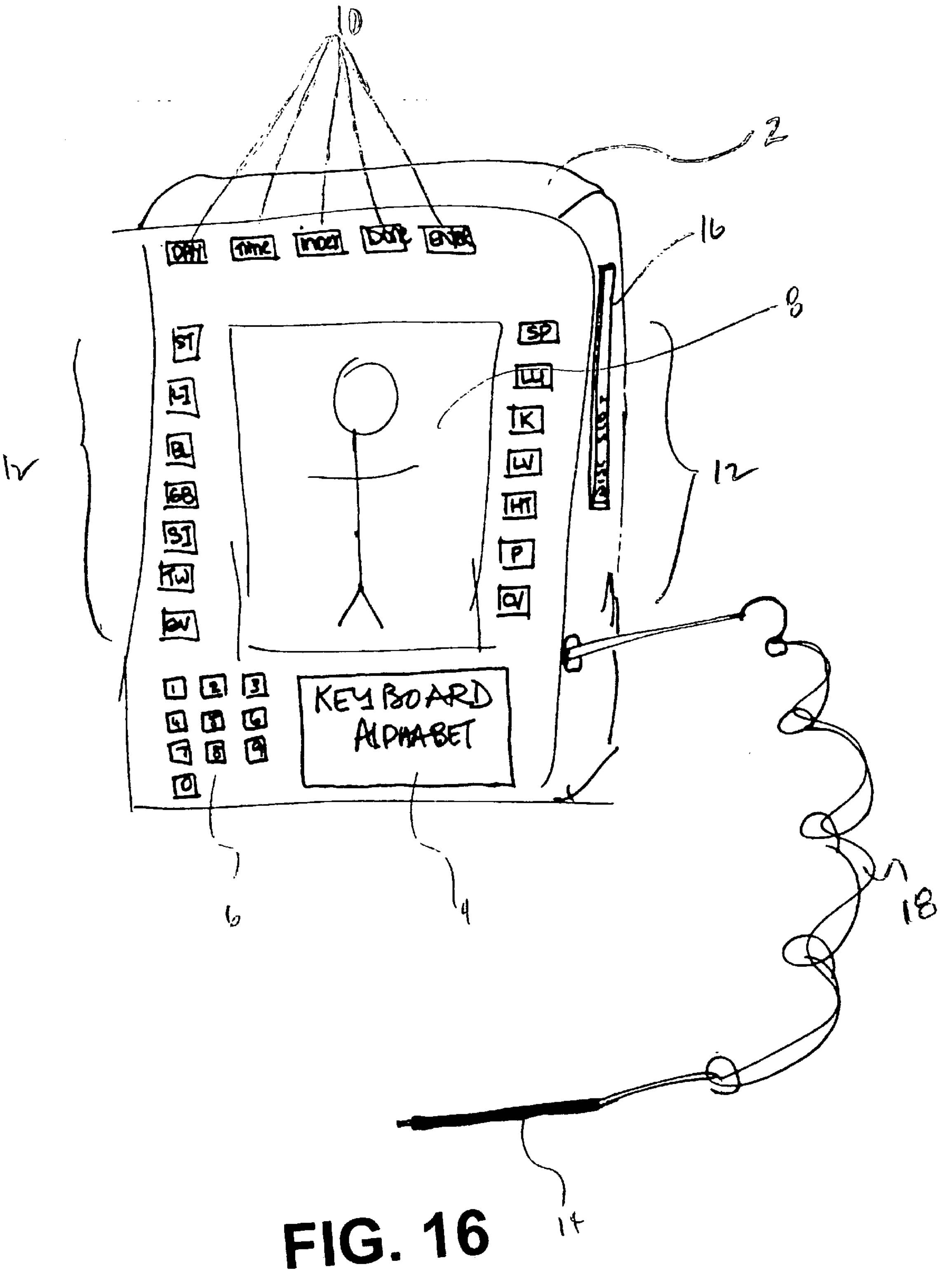
FIG. 16 is an overview of an interactive monitoring device for practicing the process of the subject invention.

However, it has been discovered by the inventor hereof that articulation of these twenty-four points together with five additional points, as discussed below and shown in the drawings, at certain times in a women's cycle in an ongoing fashion have beneficial regulatory effects on women's ensuing cycles, and, at times, immediate improvement has even been demonstrated. A regime has thus been developed, and is identified in current formulation in Sets 1, 2 and 3 and in the Short Version below, to utilize the discovered effect in a systematic fashion. A portable, interactive device is also shown in FIG. 16, and a block diagram of certain of its components shown in FIG. 17.

It is important to recognize that the process requires that the twenty-four points (plus five additional) be identified on a person's body, as shown in FIGS. 1–15, and then that these points be properly articulated. Finding an acupressure point is likened to finding the reflex point on a knee. First the general location is identified. Then, the person tries tapping the knee a few times. Suddenly, when a hit occurs, the knee uncontrollably jerks. After frequently tapping and finding, at some point, location becomes easier and easier, almost automatic, indeed almost itselve reflexive.

Likewise, to practice the instant invention, the points must first be generally localized in accordance with the FIGS. 1–15, and then the same "hunt and peck" feeling as searching for the knee reflex point is applied. Once the particular point is "found" and pressed, there will be some feeling of pain or discomfort. If, however, the point is located but no real sensation emerges, it is likely that there is an energetic block or gap between points. Also, it is best if the points are articulated directly (i.e., without a barrier like clothing).

Generally, once the point is found, articulation (intensity and direction) are best identified by the person employing the instant process and her own internal feedback. To "tonify" or draw energy into the body, a point is massaged in a clockwise direction. To "sedate" or reduce energy in/to the body, a counterclockwise direction is employed. Articulation of the points, once the identity and sequence is established as disclosed herein, should be done in accordance with generally recognized massage and acupressure therapy.

Figure 1:
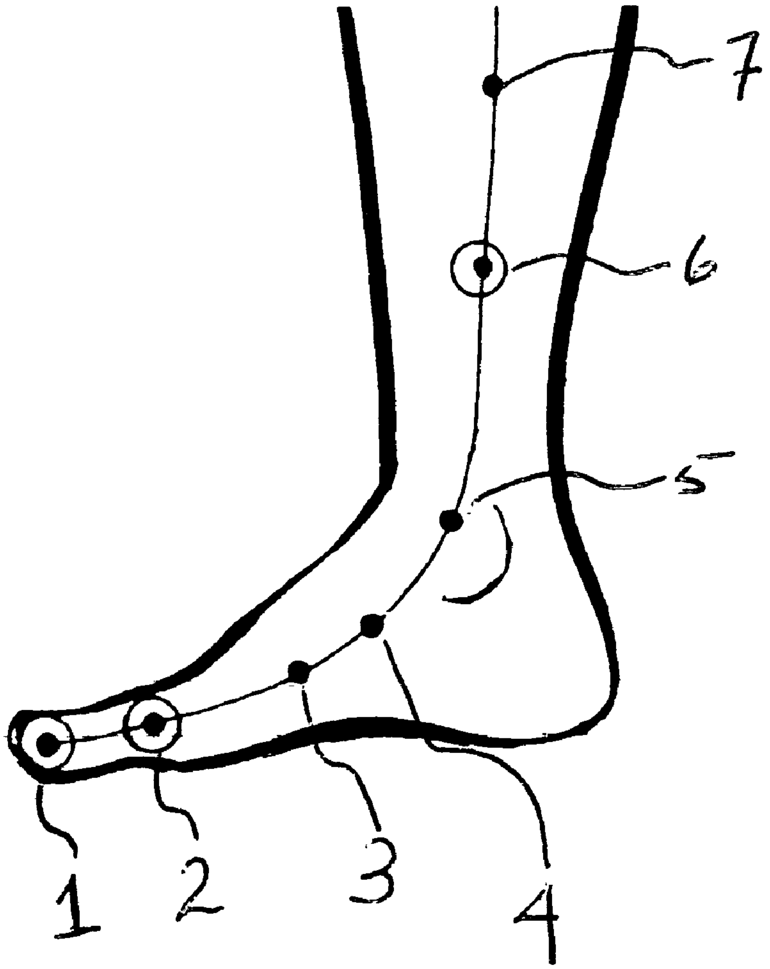
FIG. 1 is a diagrammatical representation of a number of accupressure points that are involved in regulation of the energy flow of the spleen, and in particular certain points that are articulated in accordance with the invention.

In FIG. 1, seven points are shown, numbered 1 through 7, that regulate some of the energy flows associated with the spleen organ which energetically governs the sexual energy, although physically it is responsible for health of the body's immune system. Three of these points, numbered 1, 2 and 6 were originally classified as Forbidden Points, since massage of these points at the times indicated below during a pregnancy, could cause a miscarriage.

| Point Number | Oriental Name | Forbidden From Month: |
|---|---|---|
| 1 | Hidden White | 1 |
| 2 | Great Capital | 1 |
| 6 | Three Yin Crossing | 9 |

Figure 2:
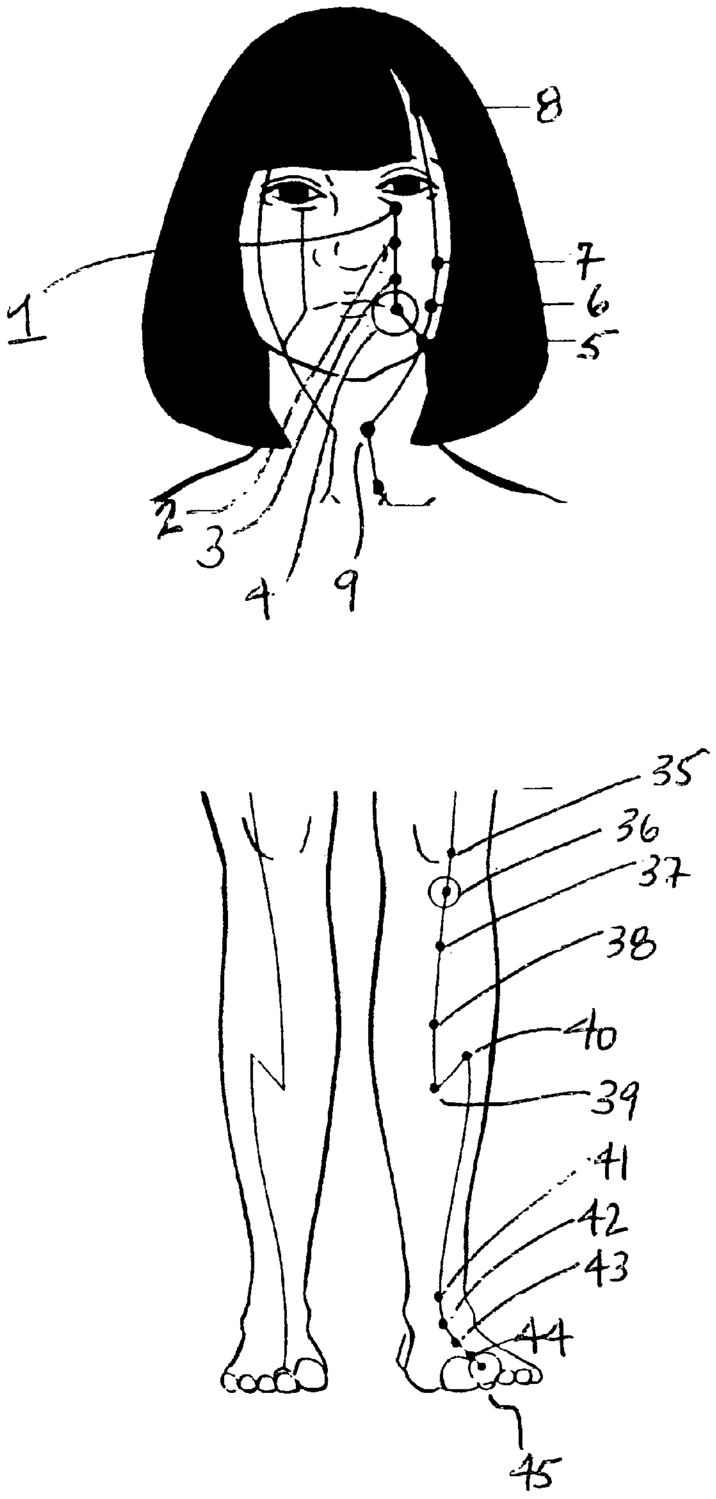
FIG. 2 is a diagrammatical representation of a number of accupressure points that are involved in regulation of the energy flows associated with the stomach, and in particular certain points that are articulated in accordance with the invention.

FIG. 2 shows points 1 through 9, and 35 to 45 which are partially responsible for regulating the energy flows typically associated with the stomach organ, and further show three individual points 4, 36 and 45 which were forbidden for articulation for pregnant women in the months of their pregnancy indicated below.

| Point Number | Oriental Name | Forbidden From Month: |
|---|---|---|
| 4 | Earth Granary | 5 |
| 36 | Leg Three Miles | 8 |
| 45 | Severe Mouth | 6 |

Figure 3:
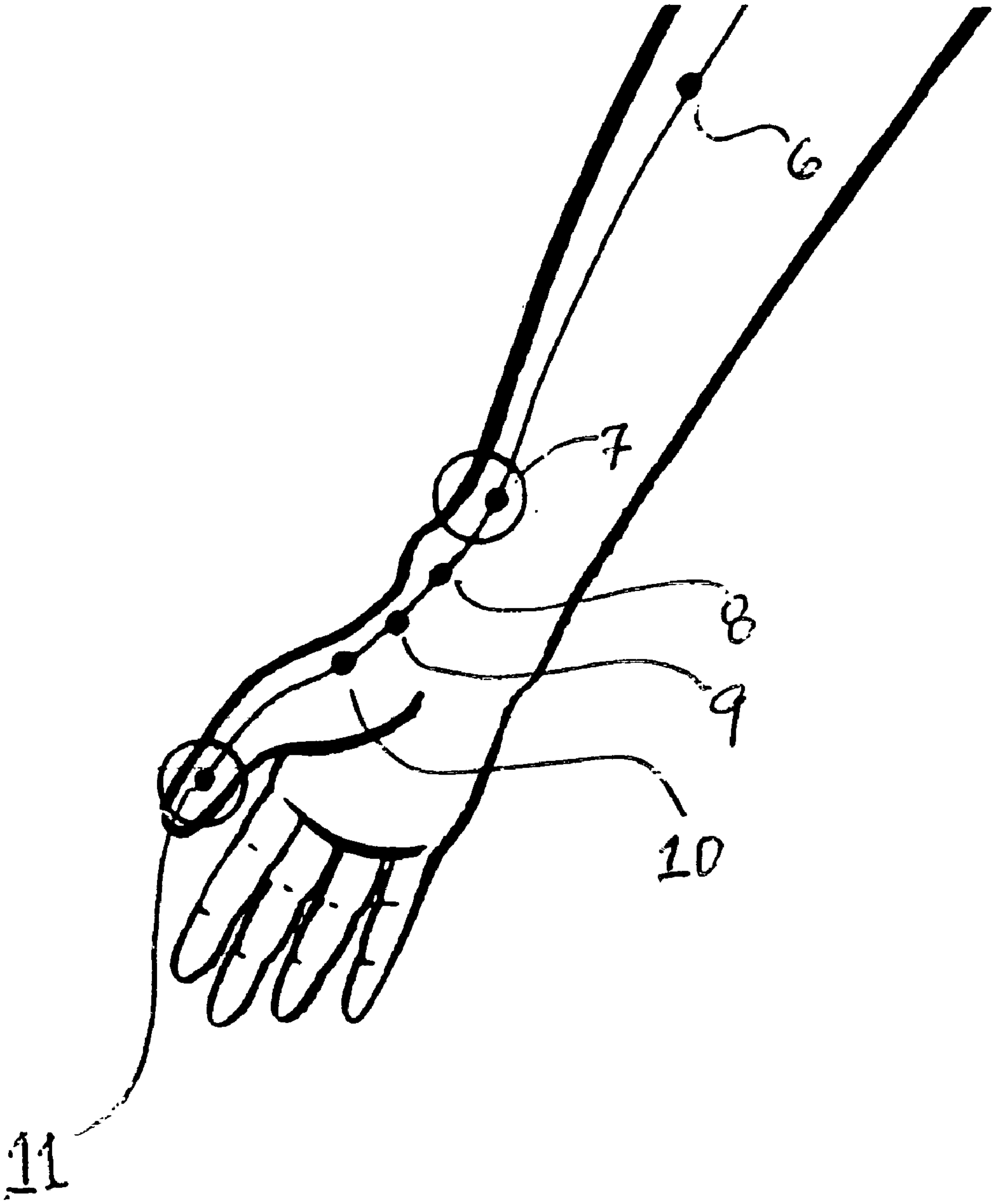
FIG. 3 is a diagrammatical representation of a number of accupressure points that are involved in regulation of the energy flows associated with the lung, and in particular certain points that are articulated in accordance with the invention.

In FIG. 3, points 6 through 11 are shown and are typically associated with the energy flows of the lung as an organ. Points 7 and 11 have been generally recognized as forbidden for articulation during pregnancy in the months indicated below.

| Point Number | Oriental Name | Forbidden From Month: |
|---|---|---|
| 7 | Broken Sequence | 6 |
| 11 | Little Merchant | 7 |

Figure 4:
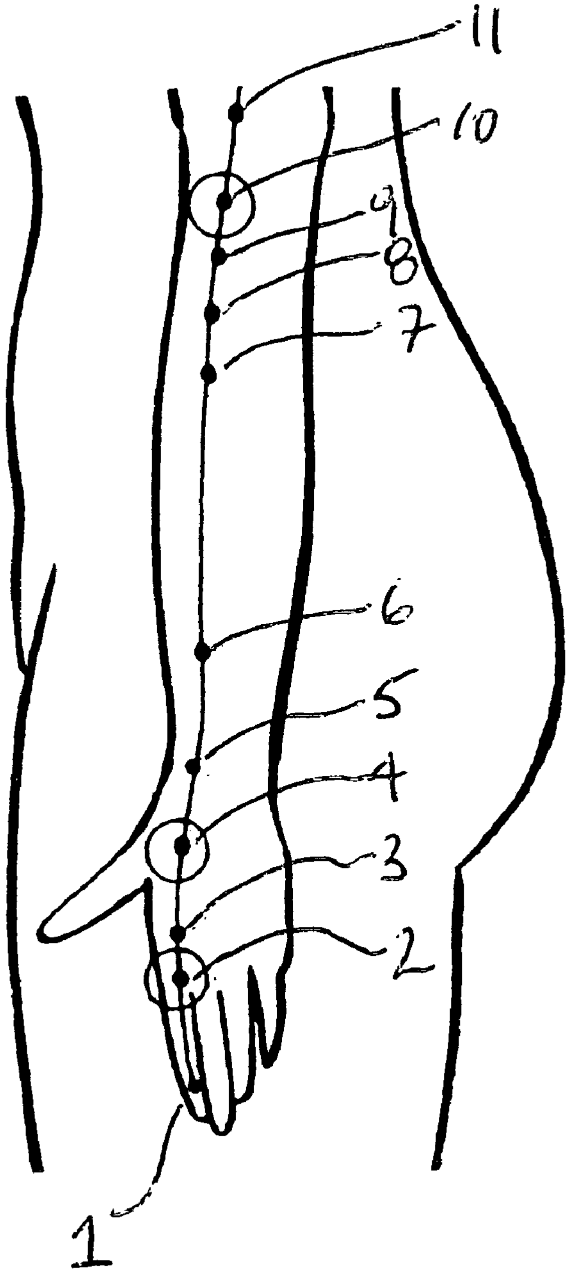
FIG. 4 is a diagrammatical representation of a number of accupressure points that are involved in regulation of the energy flows associated with the large intestine, and in particular certain points that are articulated in accordance with the invention.

In FIG. 4, points 1 through 11 are shown and are typically associated with the energy flow large intestine as an organ. Points 2, 4 and 10 were taught to be forbidden points for ulation during pregnancy in the months indicated below.

| Point Number | Oriental Name | Forbidden From Month: |
|---|---|---|
| 2 | Second Space | 9 |
| 4 | Ho Ku or Tiger's Mouth or Joining the Valleys or Great Eliminator | 1–9 |
| 10 | Arm Three Miles | 9 |

Figure 5:
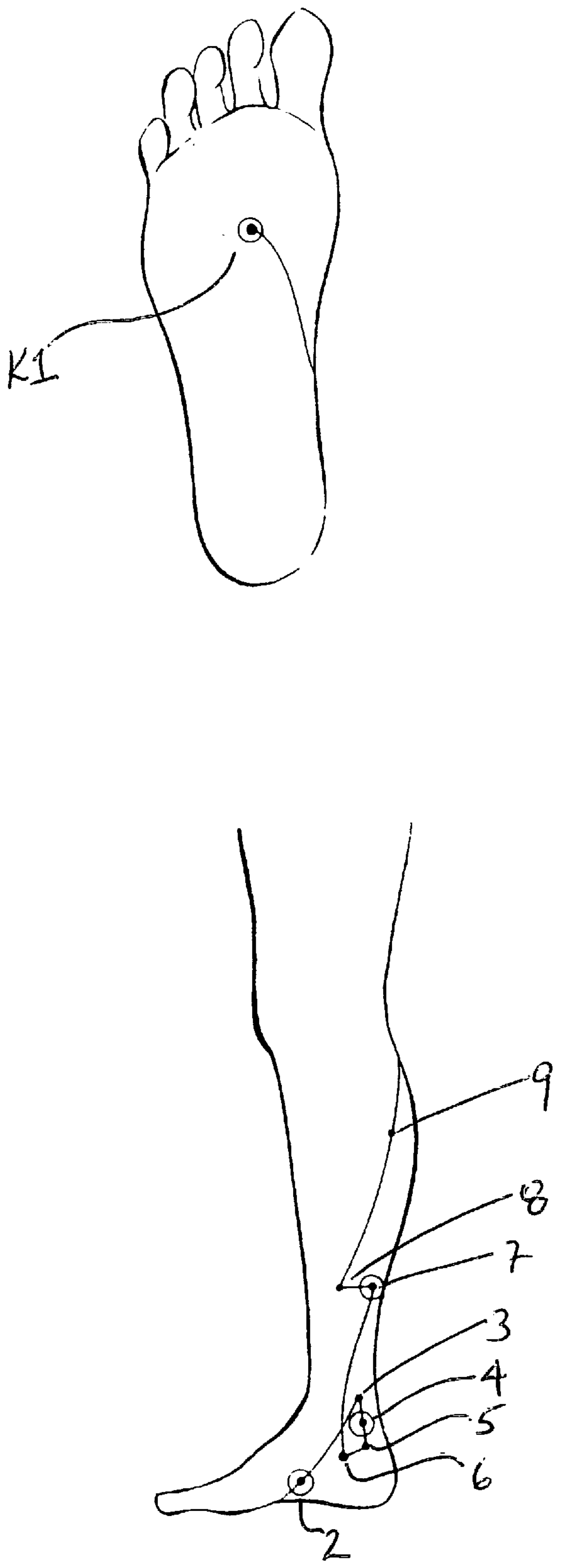
FIG. 5 is a diagrammatical representation of a number of accupressure points that are involved in regulation of the energy flows associated with the kidney, and in particular certain points that are articulated in accordance with the invention.

FIG. 5 shows the acupressure points K1 and 2 through 9 which are typically associated the energy flows of the kidney as an organ. Four of these points, K1, and 2, 4 and 7 have contra-indicated during pregnancy as shown in the chart below.

| Point Number | Oriental Name | Forbidden From Month: |
|---|---|---|
| 1 | Bubbling Spring | 1 & 8 |
| 2 | Blazing Valley or Dragon in the Abyss/Spring | 8 |

-continued

| Point Number | Oriental Name | Forbidden From Month: |
|---|---|---|
| 4 | Great Bell | 3 |
| 7 | Returning Flow | 8 |

Figure 6:
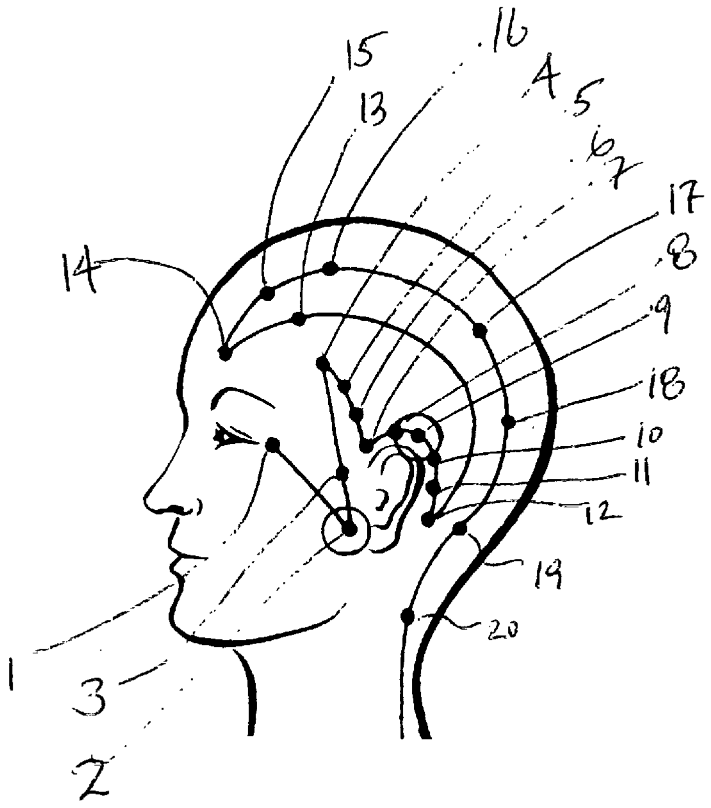
FIG. 6 is a diagrammatical representation of a number of accupressure points that are involved in regulation of the energy flows associated with the gall bladder, and in particular certain points that are articulated in accordance with the invention.
Figure 6:
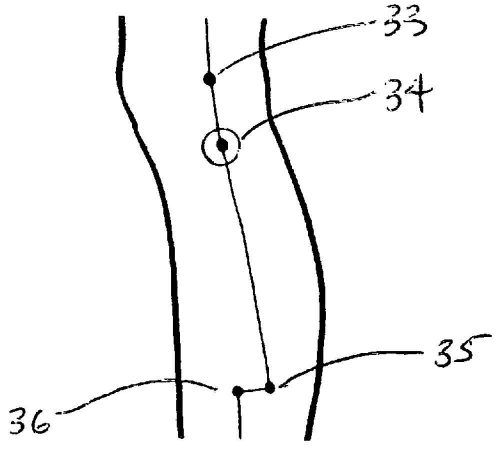

FIG. 6 shows the acupressure points 1 through 20 and 33 through 36 which are typically iated with the energy flows of the gallbladder as an organ. Those points forbidden during pregnancy, 2, 9 and 34 are circled in FIG. 6 and specified below.

| Point Number | Oriental Name | Forbidden From Month: |
|---|---|---|
| 2 | Hearing Assembly | 1 |
| 9 | Heaven Rushing | 4 |
| 34 | Yang Mound Spring | 2 |

Figure 7:
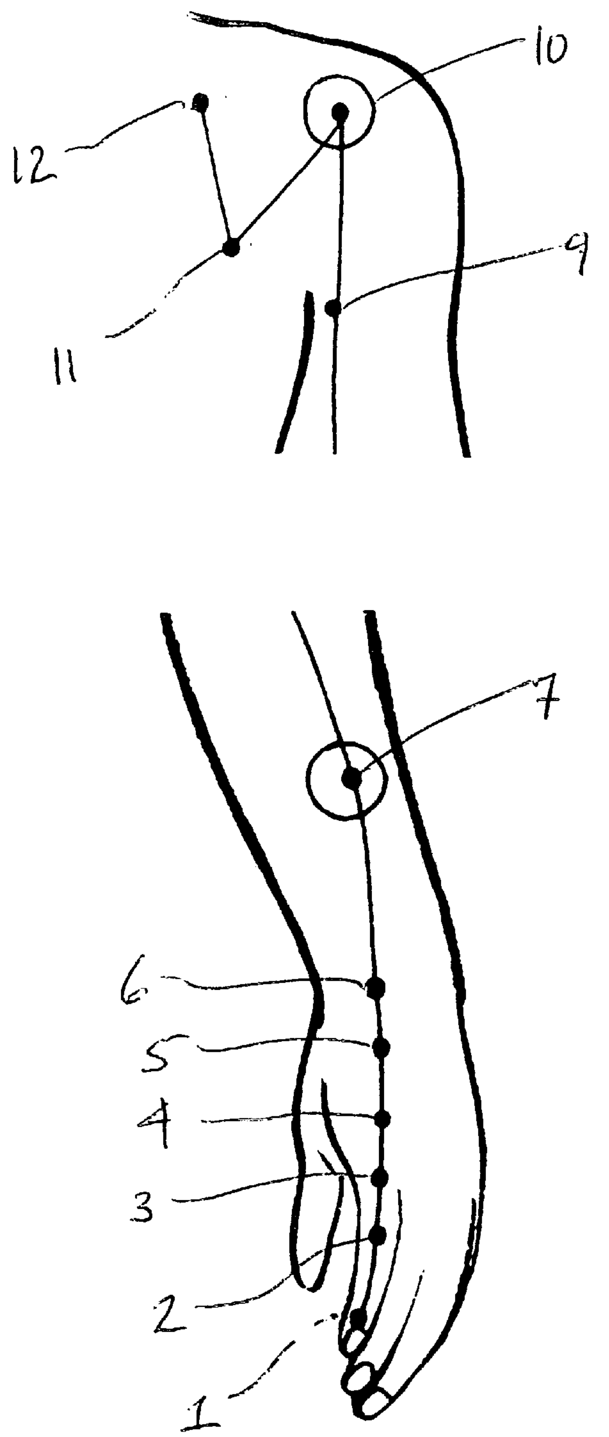
FIG. 7 is a diagrammatical representation of a number of accupressure points that are involved in regulation of the energy flows associated with the small intestine, and in particular certain points that are articulated in accordance with the invention.

FIG. 7 shows the acupressure points 1 through 7 and 9 through 12 which are typically associated with the energy flows of the small intestine as an organ. Those points forbidden during pregnancy, 7 and 10 are circled in FIG. 7, and specified below.

| Point Number | Oriental Name | Forbidden From Month: |
|---|---|---|
| 7 | Regulating Branch or Branch to the Correct | 6 |
| 10 | Shoulder Blade | 6 |

Figure 8:
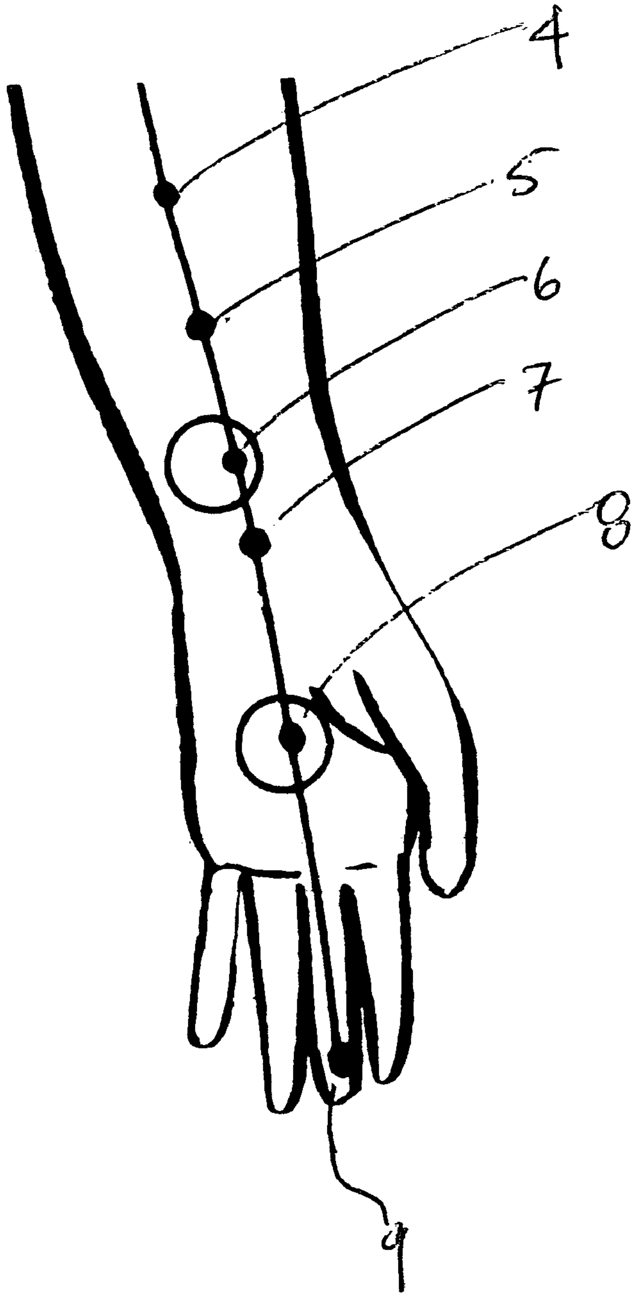
FIG. 8 is a diagrammatical representation of a number of accupressure points that are involved in regulation of the energy flows associated with the pericardium, and in particular certain points that are articulated in accordance with the invention.

FIG. 8 shows the acupressure points 4 through 8 which are typically associated with the energy flows of the pericardium energy flow. Those points forbidden during pregnancy, 6 and 8 are circled in FIG. 8 and specified below.

| Point Number | Oriental Name | Forbidden From Month: |
|---|---|---|
| 6 | Inner Frontier Grate | 4 |
| 8 | Palace of Weariness | 3 |

Figure 9:
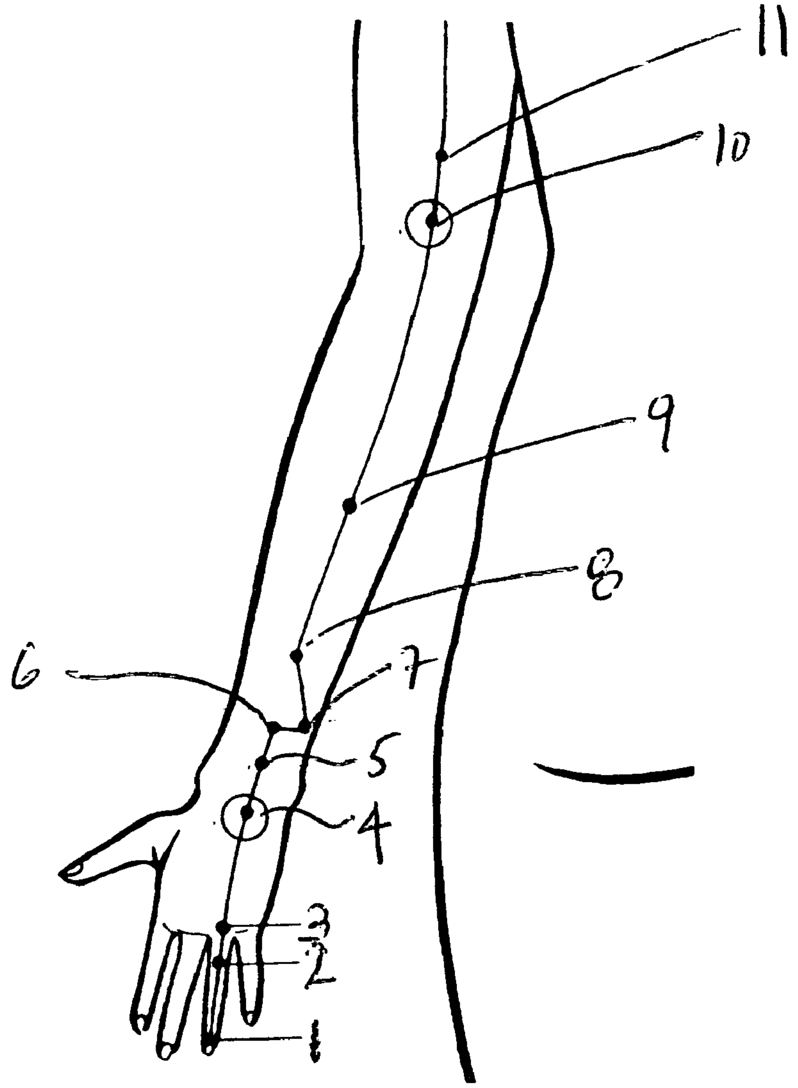
FIG. 9 is a diagrammatical representation of a number of accupressure points that are involved in regulation of the energy flows associated with the body in general (called "triple warmer"), and in particular certain points that are articulated in accordance with the invention.

FIG. 9 shows the accupressure points 1 through 11 which are typically associated with the energy flows of the so-called triple warmer, which is the flow responsible for regulating all other flows in the body. Those points forbidden during pregnancy, 4 and 10 are circled in FIG. 9 and specified below.

| Point Number | Oriental Name | Forbidden From Month |
|---|---|---|
| 4 | Yang Pond | 3 |
| 10 | Heavenly Well | 3–5 |

Accordingly, these twenty four points (Spleen 1, 2, 6; Stomach 4, 36, 45; Lung 7, 11; Large Intestine 2, 4, 10; Kidney 1, 2, 4, 7; Gallbladder 2, 9, 34; Small Intestine 7, 10; Pericardium 6, 8; Triple Warmer 4, 10) are typically forbidden. Articulation in accordance with the regime disclosed herein has, however, various beneficial functions.

Figure 10:
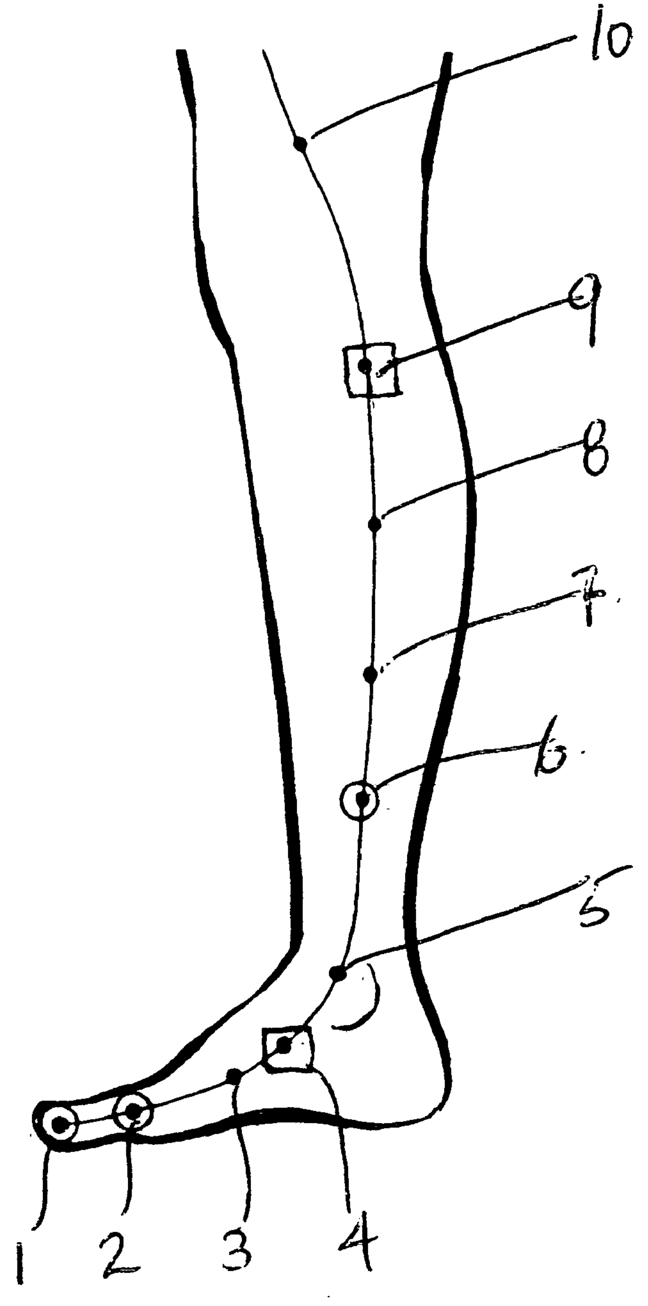
FIG. 10 is a diagrammatical representation of a number of accupressure points that are involved in regulation of the energy flows associated with the spleen, and in particular certain points that are articulated in accordance with the invention.

Certain additional points are not traditionally identified as forbidden during pregnancy, but are equally disregarded in treatment of women because of the concern associated with an adverse effect on pregnancy as a result of the clearing out effect and relaxation of the womb which consequent from their articulation. These additional points have herein been discovered to have beneficial effects when articulated in accordance with the procedures set forth herein, for the following varied reasons:

Spleen 4, shown in FIG. 10, is helpful in relieving cramps, since it has been found to assist in relaxing the uterus.

Spleen 9, also shown in FIG. 10, has been found herein to be helpful in relieving swelling, edema, and generally has a regulating effect on the spleen.

Figure 11:
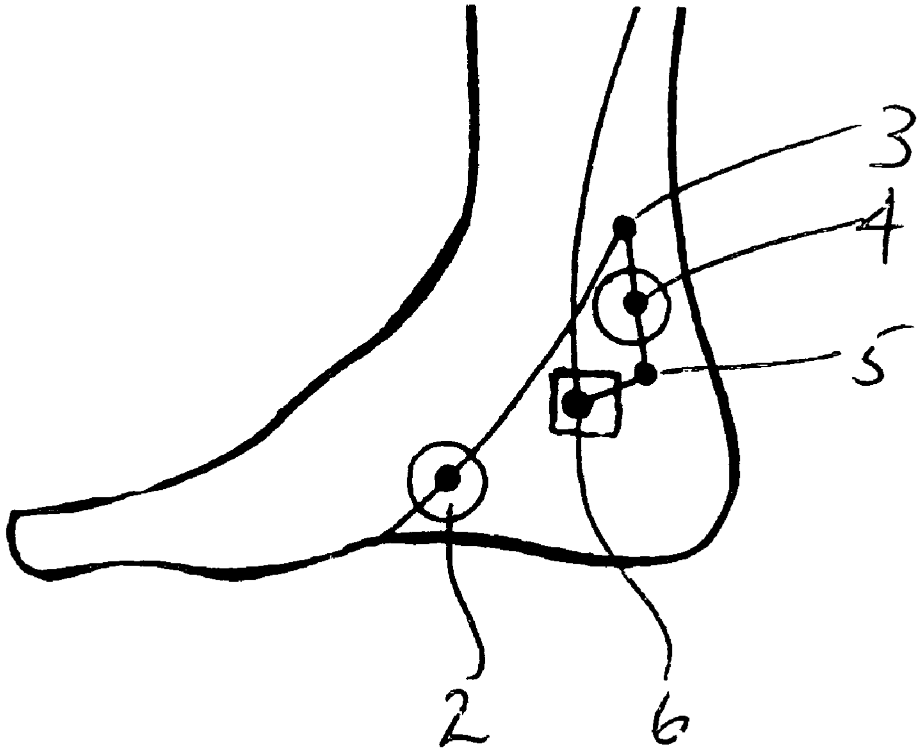
FIG. 11 is a diagrammatical representation of a number of accupressure points that are involved in regulation of the energy flows associated with the kidney, and in particular certain points that are articulated in accordance with the invention.

Kidney 6, as shown in FIG. 11, has been found to have a strengthening effect on the uterus and is good for prolapse. It also has been found to assist in relieving cramps, swelling, and helps to clear up irregular menstruation.

Figure 12:
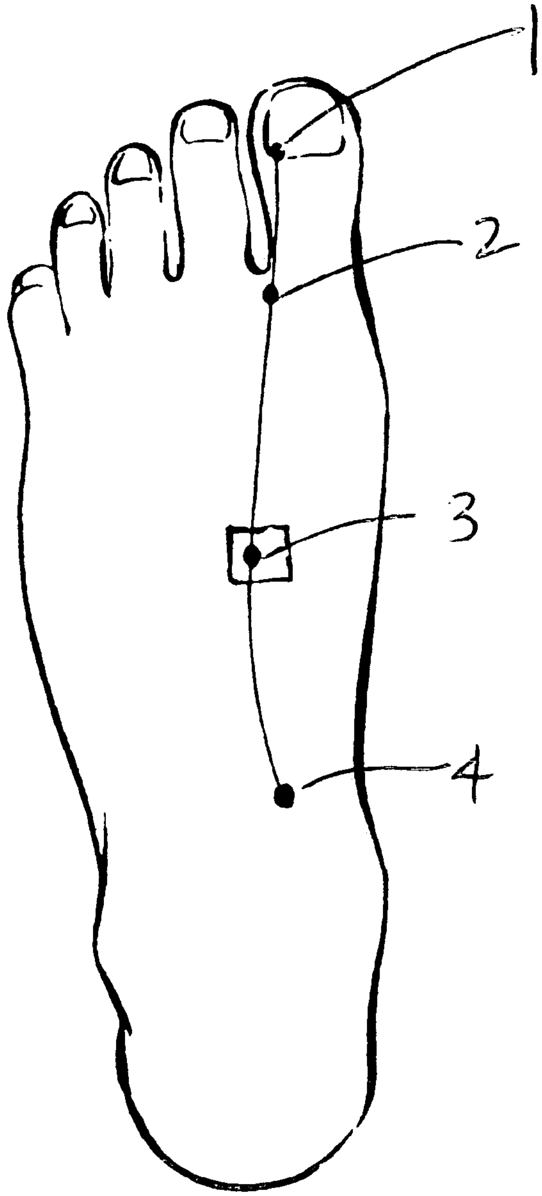
FIG. 12 is a diagrammatical representation of a number of accupressure points that are involved in regulation of the energy flows associated with the liver, and in particular certain points that are articulated in accordance with the invention.

Liver 3, as shown in FIG. 12, is known for opening the womb (dilating the cervix). Since articulation thereof assists in reducing edema and relieving constipation, articulation will also help reduce pressure pains against the uterus.

Figure 13:
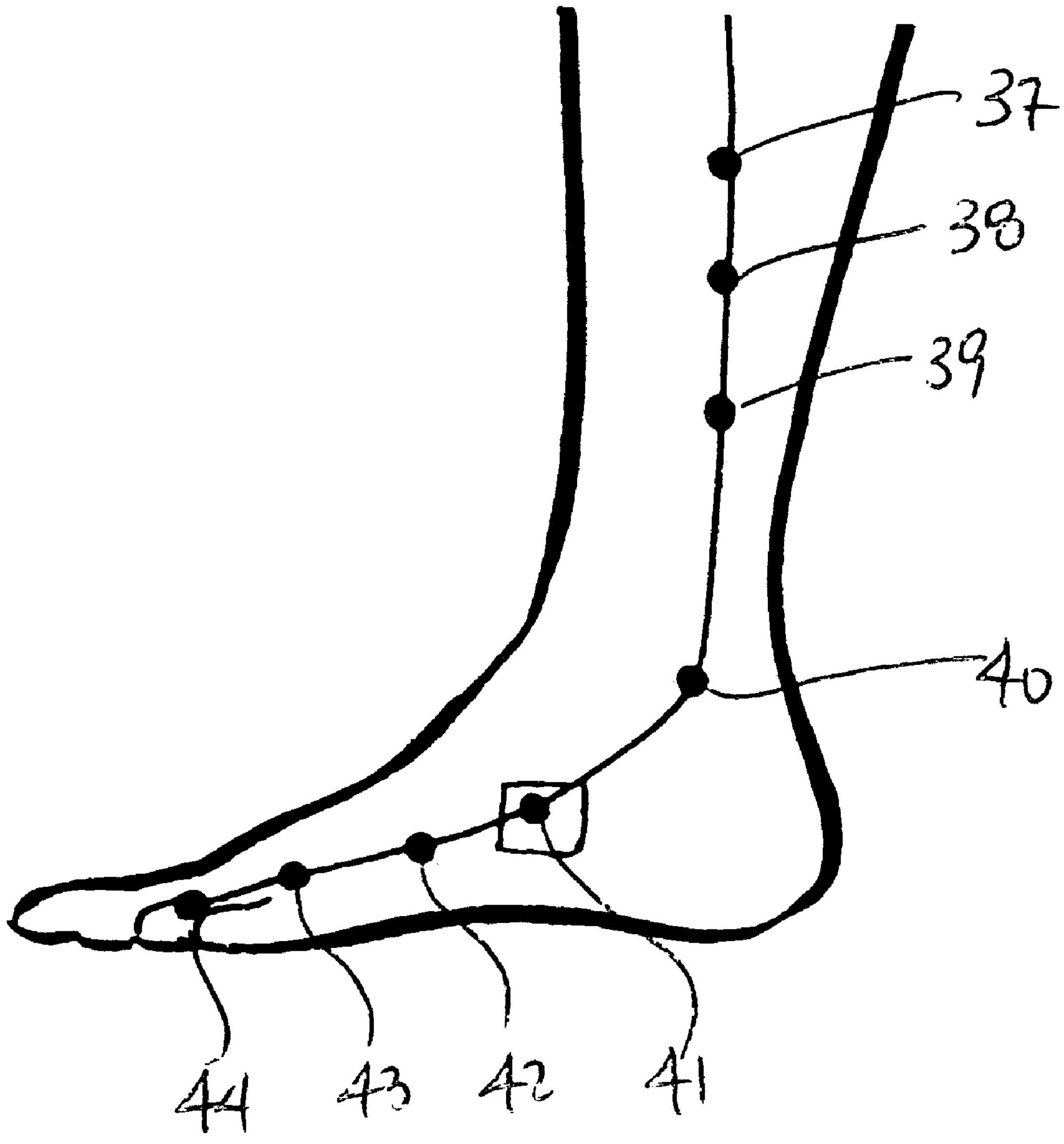
FIG. 13 is a diagrammatical representation of a number of accupressure points that are involved in regulation of the energy flows associated with the gall bladder, and in particular certain points that are articulated in accordance with the invention.
Figure 14:
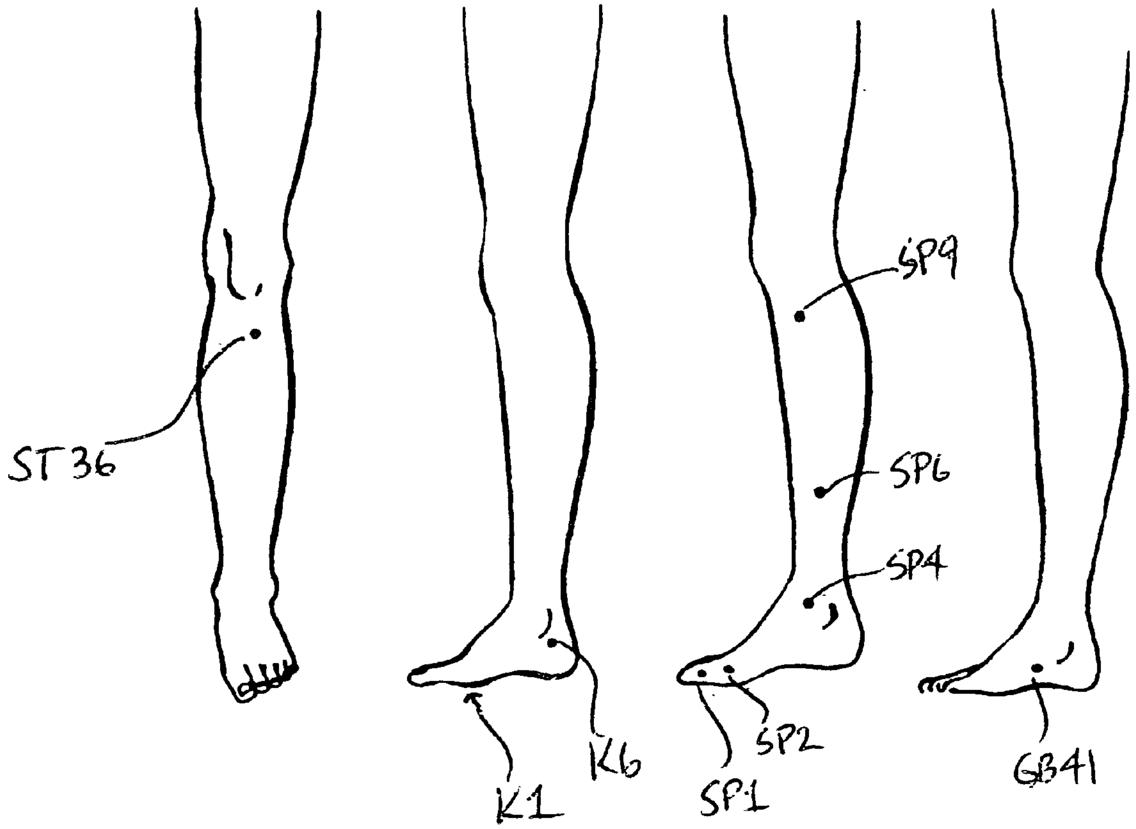
FIG. 14 is a summarial, diagrammatical representation of a number of accupressure points that are articulated in accordance with a "short version" of the system of the invention, for improving contraception.
Figure 15:
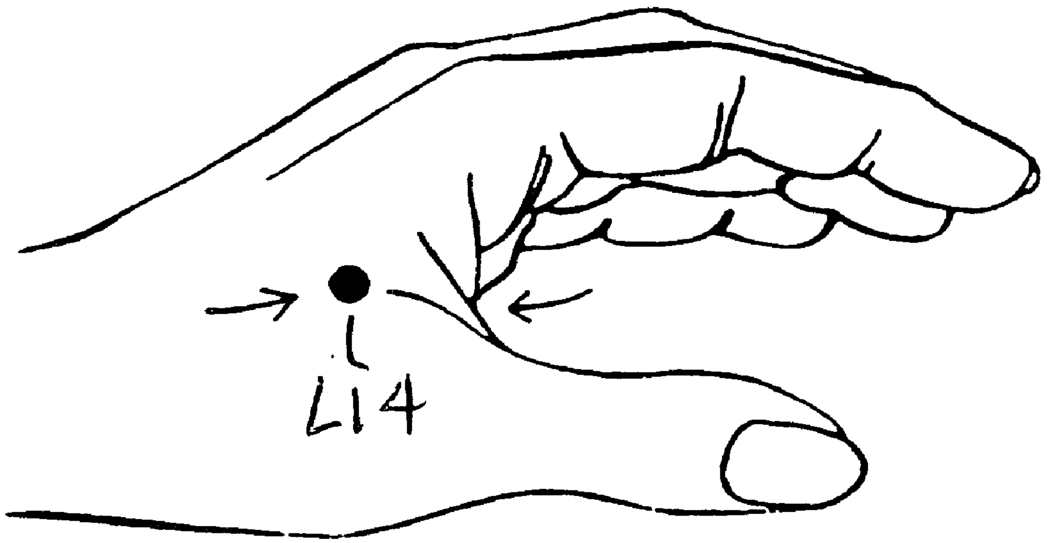
FIG. 15 is a diagrammatical representation of large intestine accupressure point 4, which is articulated in accordance with the "short version" of the system of the invention, all as more fully described below.

Gallbladder 41, as shown in FIG. 13 serves to eliminate pain and swelling in the breasts and to reduce abdominal distention. It has been discovered herein that a good working of this point will, over time, help stop premenstrual pain, tenderness, and swelling of the breasts in the subsequent cycle.

It should be appreciated that articulation of the 24 points typically ignored or taught away by the prior art, in the manner set forth herein, to regulate a women's cycle during menstruation, is enhanced by articulation of the additional points which are discussed in connection with FIGS. 10–13.

FIG. 10 thus shows a larger number of acupressure points associated with the energy s of the spleen (see also FIG. 1), and in particular indicates two additional points which should be articulated in accordance with the instant invention, and are identified in the table, below.

FIG. 10 also shows points 3, 5, 7, 8 and 10 which are not involved in this procedure but which are identified for purposes of clarity as follows: Point 3: Supreme White; point 5: Shang Hill; point 7: Leaking Valley; point 8: Earth's Crux; and point 10: Sea of Blood.

| Point Number | Oriental Name |
|---|---|
| 4 | Prince's Grandson |
| 9 | Yin Mound Spring |

Likewise, FIG. 11 shows a larger number of acupressure points typically associated with the energy flow of the kidney (see also FIG. 5), and in particular indicates one additional points which should be articulated in accordance with the instant invention, and is identified in the table, below.

| Point Number | Oriental Name |
|---|---|
| 6 | Shining Sea |

FIG. 12 shows a number of acupressure points typically associated with the energy flow of liver, and in particular indicates one additional point which should be articulated in accordance with the instant invention, and is identified in the table below.

| Point Number | Oriental Name |
|---|---|
| 3 | Supreme Rushing or Great Pouring |

FIG. 13 shows a number of acupressure points typically associated with the energy flow of the gallbladder, and are additional to the ones shown in FIG. 6. FIG. 13 also shows one point which should be articulated in addition to those 24 forbidden, which is identified below.

| Point Number | Oriental Name |
|---|---|
| 41 | Foot Overlooking Tears |

Menstruation typically occurs for a three day interval, and thus the following sets are dated to be followed each day. That is, set one should occur on the first day of bleeding, set n the second, and set three on third. Articulation of each point should occur during the dated Peak Time for that point, in the order indicated, and for a duration of 3 to 5 minutes per set. Each point that is directly indicated (with no parenthesis) refers to a point in the active FIGS. 1–9 which are together circled thereon as those points typically forbidden for ulation by women. Each point that is indicated in parenthesis refers to an additional point covered herein, and indicated in the respective one of FIGS. 10–13.

| Flow | Point | Peak Time |
|---|---|---|
| | Set One | |
| Large Intestine (FIG. 4) | 4 | 5–7 a.m. |
| Spleen (FIG. 1, FIG. 10) | 1, 2, (4, 9) | 9–11 a.m. |
| Kidney (FIG. 5, FIG. 11) | 1, 4, (6) | 5–7 p.m. |
| Pericardium (FIG. 8) | 8 | 7–9 p.m. |
| Triple Warmer (FIG. 9) | 4, 10 | 9–11 p.m. |
| Gallbladder (FIG. 6, FIG. 13) | 2, 34, (41) | 11 p.m.–1 a.m. |
| Liver (FIG. 12) | (3) | 1–3 a.m. |
| | Set Two | |
| Lung (FIG. 3) | 7 | 3–5 a.m. |
| Large Intestine (FIG. 4) | 4 | 5–7 a.m. |
| Stomach (FIG. 2) | 4, 45 | 7–9 a.m. |
| Small Intestine (FIG. 7) | 7, 10 | 1–3 p.m. |
| Kidney (FIG. 5) | 4 | 5–7 p.m. |
| Pericardium (FIG. 8) | 6 | 7–9 p.m. |
| Triple Warmer (FIG. 9) | 10 | 9–11 p.m. |
| Gallbladder (FIG. 6) | 9 | 11 p.m.–1 a.m. |
| | Set Three | |
| Lung (FIG. 3) | 11 | 3–5 a.m. |
| Large Intestine (FIG. 4) | 2, 4, 10 | 5–7 a.m. |
| Stomach (FIG. 2) | 36 | 7–9 a.m. |

-continued

| Flow | Point | Peak Time |
|---|---|---|
| Spleen (FIG. 1) | 6 | 9–11 a.m. |
| Kidney (FIG. 5) | 1, 2, 7 | 5–7 p.m. |

It should be appreciated and understood that articulation of the foregoing points can occur during the time intervals indicated, since those time intervals are associated with peak energy flows and thus are preferred. For working women, the sets can be divided between morning and evening and thereby completed with a level of convenience.

Alternatively, a Short Version can be followed in order for a woman to achieve a monthly clear out. Articulation in accordance with the Short Version, below, can, by the third month, minimize PMS problems or troubles.

| Short Version | | |
|---|---|---|
| Flow | Point | Peak Time |
| Spleen (FIG. 10) | 1, 2, 4, 6, 9 | 9–11 a.m. |
| Stomach (FIG. 2) | 36 | 7–9 a.m. |
| Large Intestine (FIG. 4) | 4 | 5–7 a.m. |
| Kidney (FIG. 11) | 1, 6 | 5–7 p.m. |
| Gall Bladder (FIG. 13) | 41 | 11 p.m.–1 a.m. |

The Short Version should be worked every day during a woman's period until the bleeding, stops, and is for women who, for one reason or another simply cannot fit the three sets of points into their lives. At absolute minimum, Large Intestine 4 and Spleen 6 should be worked a few times per day while the woman's period is in progress.

A contraceptive method can also be employed. While no guarantees exist, the risk is only of pregnancy. The following sequence is followed three days before a woman's period is due (day 25 is indicated for a regular 28 day cycle) and the points can be found in FIGS. 14 and 15:

| Day 25 | | |
|---|---|---|
| Flow | Point | Peak/Low Time |
| Spleen (FIG. 14) | 1, 2, 4, 6, 9 | 9–11 a.m./p.m. |
| Stomach (FIG. 14) | 36 | 7–9 a.m./p.m. |
| Large Intestine (FIG. 15) | 4 | 5–7 a.m./p.m. |
| Kidney (FIG. 14) | 1, 6 | 5–7 p.m./a.m. |
| Gallbladder (FIG. 14) | 41 | 11 p.m./a.m.–1 a.m./p.m. |

All of the foregoing points, with the exception of LI 4, are found on the lower leg, from the knee to the ball of the foot. If the woman is at work on day 25, it is recommended that she work the less obvious flows, like LI 4. At the end of the day, she can finish with the Spleen, Stomach, Kidney and Gallbladder Flow points. Care must be extended to the low hours between 9 and 11 p.m. for Spleen because the object of this technique is to disperse energe massaging the points in a counterclockwise direction. During the low hours, a flow is at its most vulnerable, and one can easily disperse more energy by working the points at this time.

The foregoing massage is continued on the remaining days prior to the period, i.e., for the example given of a 28 day period, commencing on day 25, and continuing for days 26, 27 and 28, the points indicated above are articulated as indicated above until bleeding is commenced.

Lastly, it is recommended that after bleeding commences, the normal system, as indicated above should be followed for each and every day, while bleeding.

Delaying the onset of menopause can occur by keeping Kidney, Heart and Spleen flows healthy in all aspects of daily living—free from emotional stress, nourished with wholesome nutrition. Pre-menopausal and menopausal women will benefit from tonifying the 24 Forbidden Pregnancy Points identified above once a month during the full moon, together with massaging the following additional points:

To tonify the Kidney, massage Kidney 3, 7, Bladder 23, 52, Conception Vessel 4

To tonify the Heart, massage Heart 1, 7, Spleen 6, 9, Pericardium 6, 7, Conception Vessel 17, To tonify the Spleen, massage Spleen 2, 3, Stomach 36, Bladder 20, Liver 13, and Conception Vessel 12.

These points should be worked for four days beginning a few days prior to the full moon, in the order listed, massaged in a clockwise direction to tonify, or draw energy in. This system should commence as soon as the first symptoms of menopause are observed.

In order to minimize the chances of miscarriage or to stop abnormal uterine bleeding, the following points can be worked:

Anti-Miscarriage Points

| Point Number | Oriental Name |
|---|---|
| Spleen 3 | Supreme White |
| Spleen 10 | Sea of Blood |
| Large Intestine 1 | Shang Yang or Extreme Yang |
| Bladder 15 | Heart's Hollow (Shu) |
| Bladder 17 | Diaphragm's Hollow (Shu) |
| Bladder 18 | Liver's Hollow (Shu) |
| Bladder 22 | Triple Burner's Hollow |
| Bladder 23 | Kidney's Hollow (Shu) |
| Bladder 31 | Upper Sacral Bone-Hole |
| Bladder 32 | Second Sacral Bone-Hole |
| Bladder 33 | Central Bone-Hole |
| Bladder 34 | Lower Bone-Hole |
| Conception Vessel 4 | First Gate |
| Conception Vessel 6 | Sea of Ch'i |
| Governing Vessel 20 | One Hundred Convergences |

Also, the following points can be articulated to minimize the effects and condition of edema:

| Point Number | Oriental Name |
|---|---|
| Spleen 9 | Yin Mountain Spring |
| Liver 3 | Great Surge |
| Conception Vessel 5 | Stone Gate |
| Conception Vessel 7 | Yin Intersection |

The invention, in a preferred embodiment, also includes a device for interactive stimulation and monitoring of the articulation of the Forbidden Pregnancy Points set forth above, as well as to enable or prevent miscarriage, or to alleviate symptoms of menopause.

Thus, FIG. 16 shows a device 2 in accordance with a preferred embodiment of the invention for articulating acupressure points, including the Forbidden Pregnancy Points set forth herein. In particular, device 2 possesses entry control keys including an alphabetic keyboard 4, numerical controller 6, control keys 10 and organ buttons 12. Organ buttons 12 can be yin/yang segmented. Also included can be specific day buttons for progressive sequences. Screen 8 can be used to generate an image with an observable identification of point locations. Attached to the device is a stimulator 14 and cord 18, which can light locations on screen 8 when positively placed on a point. The stimulator can also act as an ear tool. The stimulator 14 also possesses replaceable points for sanitary purposes. A disk slot 16 is provided (which can be PCMCIA port or other, depending upon the current state of the art).

Figure 17:
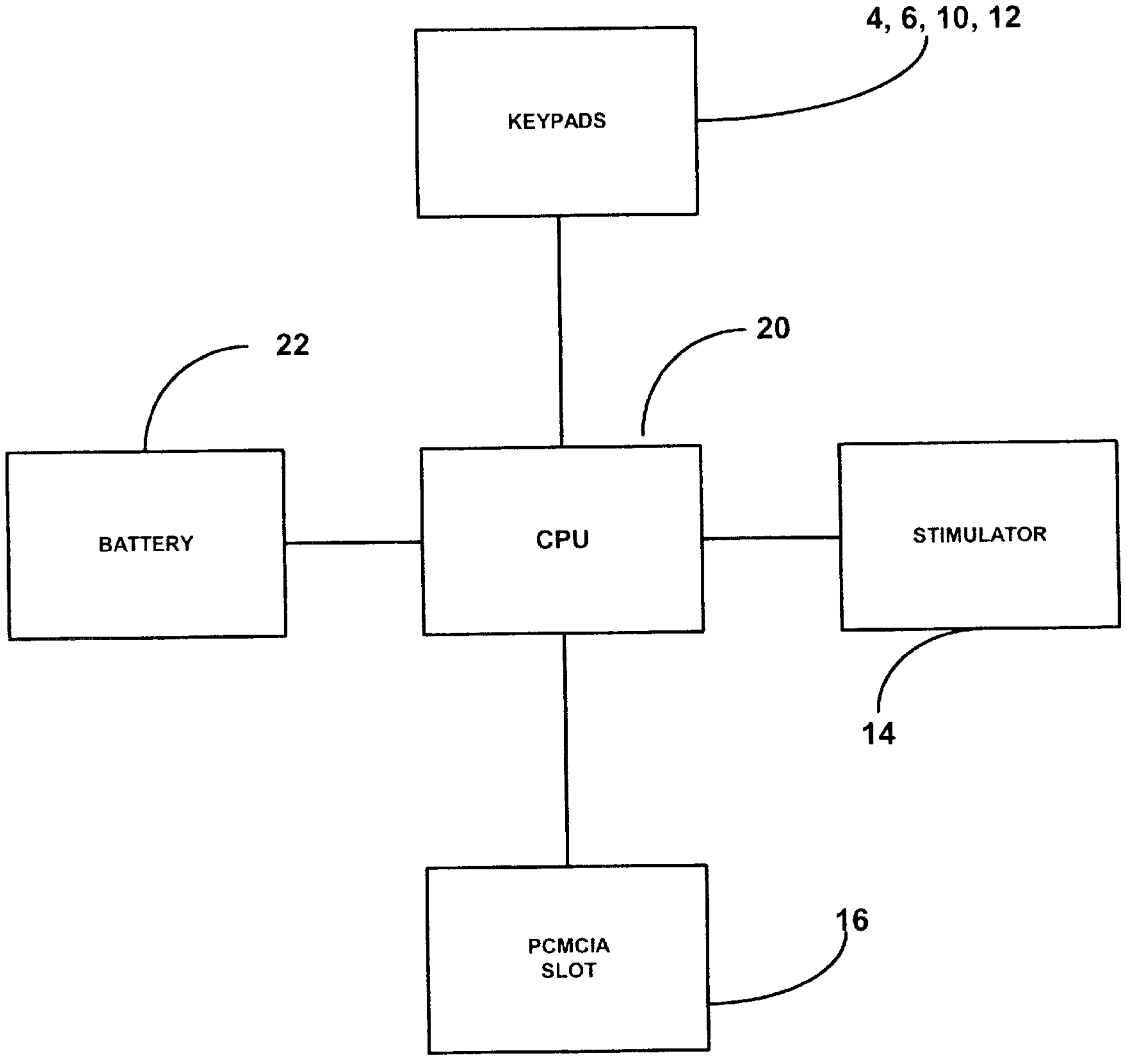
FIG. 17 is block diagram of various components contained in FIG. 16.

As shown in FIG. 17, the unit is operated by a battery 22, which attaches to a central processor 20 for performing the operations of device 2. Stimulator provides information to CPU 20, and keypads 4, 6, 10 and 12 require necessary inputs. PCMCIA slot 16 is also shown.

It should be appreciated that articulation of these points can be either by manual massage or by acupuncture stimulation, without deviation from the invention. It should also be appreciated that evidence of efficacy of the treatments set forth have been corroborated not only by the inventor, but by clients who have employed same.

It should be understood that the preferred embodiments and examples described are for illustrative purposes only and are not to be construed as limiting the scope of the present invention which is properly delineated only in the appended claims.

I claim:

1. A method for minimizing the effects of menstruation, comprising:

(a) articulating the following acupressure points at the following times on the first day of bleeding:

| Flow | Point | Peak Time |
|---|---|---|
| Large Intestine (FIG. 4) | 4 | 5–7 a.m., |
| Spleen (FIG. 1, FIG. 10) | 1, 2, 4, 9 | 9–11 a.m., |
| Kidney (FIG. 5, FIG. 11) | 1, 4, 6 | 5–7 p.m., |
| Pericardium (FIG. 8) | 8 | 7–9 p.m., |
| Triple Warmer (FIG. 9) | 4, 10 | 9–11 p.m., |
| Gallbladder (FIG. 6, FIG. 13) | 2, 34, 41 | 11 p.m.–1 a.m., and |
| Liver (FIG. 12) | 3 | 1–3 a.m.; and |

(b) articulating the following acupressure points at the following times on the second day of bleeding:

| Flow | Point | Peak Time |
|---|---|---|
| Lung (FIG. 3) | 7 | 3–5 a.m., |
| Large Intestine (FIG. 4) | 4 | 5–7 a.m., |
| Stomach (FIG. 2) | 4, 45 | 7–9 a.m., |
| Small Intestine (FIG. 7) | 7, 10 | 1–3 p.m., |
| Kidney (FIG. 5) | 4 | 5–7 p.m., |
| Pericardium (FIG. 8) | 6 | 7–9 p.m., |
| Triple Warmer (FIG. 9) | 10 | 9–11 p.m., and |
| Gallbladder (FIG. 6) | 9 | 11 p.m.–1 a.m.; and |

(c) articulating the following acupressure points at the following times on the third day of bleeding:

| Flow | Point | Peak Time |
|---|---|---|
| Lung (FIG. 3) | 11 | 3–5 a.m., |
| Large Intestine (FIG. 4) | 2, 4, 10 | 5–7 a.m., |
| Stomach (FIG. 2) | 36 | 7–9 a.m., |

-continued

| Flow | Point | Peak Time |
|---|---|---|
| Spleen (FIG. 1) | 6 | 9–11 a.m., and |
| Kidney (FIG. 5) | 1, 2, 7 | 5–7 p.m.. |

2. The method of claim 1, wherein said articulation occurs for a duration of 3 to 5 minutes.

3. The method of claim 1, wherein said articulation is by manual massage.

4. The method of claim 1, wherein said articulation is by electroacupressure.

* * * * *